United States Patent
Fernando et al.

(10) Patent No.: US 7,332,128 B2
(45) Date of Patent: *Feb. 19, 2008

(54) FIBER-OPTIC DISSOLUTION SYSTEMS DEVICES, AND METHODS

(75) Inventors: C. J. Anthony Fernando, Durham, NC (US); James E. Swon, Chapel Hill, NC (US); Henry Z. Hofer, Raleigh, NC (US)

(73) Assignee: Varian, Inc., Palo Alto, CA (US)

( * ) Notice: Subject to any disclaimer, the term of this patent is extended or adjusted under 35 U.S.C. 154(b) by 738 days.

This patent is subject to a terminal disclaimer.

(21) Appl. No.: 10/838,907

(22) Filed: May 3, 2004

(65) Prior Publication Data

US 2004/0247489 A1 Dec. 9, 2004

Related U.S. Application Data

(63) Continuation of application No. 10/014,270, filed on Nov. 7, 2001, now Pat. No. 6,764,651.

(51) Int. Cl.
G01N 21/00 (2006.01)

(52) U.S. Cl. .................. 422/100; 422/82.05; 436/164; 356/246; 356/440

(58) Field of Classification Search ................ 356/436, 356/440, 346, 244, 246; 422/82.1–82.11, 422/81, 99–104; 73/866, 866.5; 436/151, 436/164–172, 173, 181, 180, 508
See application file for complete search history.

(56) References Cited

U.S. PATENT DOCUMENTS

| 4,431,307 | A | * | 2/1984 | Suovaniemi | 356/246 |
|---|---|---|---|---|---|
| 4,528,159 | A | * | 7/1985 | Liston | 422/65 |
| 5,005,005 | A | * | 4/1991 | Brossia et al. | 340/604 |
| 5,077,481 | A | * | 12/1991 | Hoult | 250/576 |
| 5,108,703 | A | * | 4/1992 | Pfost et al. | 422/65 |
| 5,670,113 | A | * | 9/1997 | Akong et al. | 422/63 |
| 5,804,453 | A | * | 9/1998 | Chen | 436/518 |

(Continued)

FOREIGN PATENT DOCUMENTS

JP 58-85160 * 5/1983

(Continued)

Primary Examiner—Walter Griffin
Assistant Examiner—Imran Akram
(74) Attorney, Agent, or Firm—Bella Fishman; David Gloekler

(57) ABSTRACT

A dissolution system provides remote flow cells integrated into a manifold device. The manifold device communicates with liquid input and output lines associated with each flow cell, as well as fiber-optic input and output lines associated with each flow cell. Liquid samples are respectively drawn from dissolution vessels, optically-related measurements are taken, and the samples are thereafter returned their respective vessels. The manifold device can be adapted to receive probe-type instruments that incorporate the fiber-optics, wherein each probe-type instrument is associated with each flow cell. Alternatively, each corresponding pair of fiber-optic input and output lines are disposed in opposing, optically-aligned relation and probe-type instruments are not used. The gap between the ends of the opposing fiber-optic lines provides a light path across the corresponding flow cell. Calibration procedures using blank and/or standard media are performed using the same flow cells, with provisions made for bypassing the vessels in which the samples to be analyzed are held.

22 Claims, 8 Drawing Sheets

U.S. PATENT DOCUMENTS

| | | | |
|---|---|---|---|
| 6,008,055 A * | 12/1999 | Zhu et al. | 436/172 |
| 6,060,024 A * | 5/2000 | Hutchins et al. | 422/81 |
| 6,069,694 A * | 5/2000 | VonBargen | 356/246 |
| 6,083,763 A * | 7/2000 | Balch | 506/9 |
| 6,174,497 B1 * | 1/2001 | Roinestad et al. | 422/82.05 |
| 6,396,584 B1 * | 5/2002 | Taguchi et al. | 356/436 |
| 6,514,933 B1 * | 2/2003 | Young et al. | 512/1 |
| 6,519,032 B1 * | 2/2003 | Kuebler et al. | 356/337 |
| 6,580,507 B2 * | 6/2003 | Fry et al. | 356/436 |
| 6,764,651 B2 * | 7/2004 | Fernando et al. | 422/82.06 |
| 7,021,163 B2 * | 4/2006 | Kyne | 73/866 |
| 2002/0086340 A1 * | 7/2002 | Veerapandian et al. | 435/7.23 |

FOREIGN PATENT DOCUMENTS

| | | | |
|---|---|---|---|
| JP | 8-35917 | * | 2/1996 |
| JP | 10-26584 | * | 1/1998 |

* cited by examiner

FIBER-OPTIC DISSOLUTION SYSTEMS DEVICES, AND METHODS

RELATED APPLICATIONS

This application is a continuation of U.S. patent application Ser. No. 10/014,270 filed on Nov. 7, 2001 now U.S. Pat. No. 6,764,651 and titled "FIBER-OPTIC DISSOLUTION SYSTEMS, DEVICES, AND METHODS", which is incorporated in its entirety in this application by reference.

FIELD OF THE INVENTION

The present invention relates generally to the preparation, sampling and analyzing of soluble materials. More particularly, the present invention relates to apparatus and methods for implementing flow-through techniques and the use of fiber optics in connection with the testing of soluble materials.

BACKGROUND OF THE INVENTION

Dissolution testing is often performed as part of preparing and evaluating soluble materials such as pharmaceutical dosage forms (e.g., tablets consisting of a therapeutically effective amount of active drug carried by an excipient material). Typically, dosage forms are dropped into test vessels that contain dissolution media of a predetermined volume and chemical composition. For instance, the composition can have a pH factor or acidic concentration suitable for emulating a gastro-intestinal environment. Dissolution testing can be useful, for example, in studying the drug release characteristics of the dosage form or in evaluating the quality control of the process used in forming the dose. In order to ensure validation of the data generated from dissolution-related procedures, dissolution testing is often carried out according to guidelines approved or specified by certain entities such as United States Pharmacopoeia (USP), in which case the testing must be conducted within various parametric ranges. Important parameters include dissolution media temperature, the amount of allowable evaporation-related loss, and the use, position and speed of agitation or dosage-retention devices. Recent developments in robotics and other automating means have been applied to dissolution media preparation and sample analysis technology, and have resulted in improved procedural efficiency and data quality.

As a dosage form is dissolving in the test vessel of a dissolution system, samples of the solution can be taken at predetermined time intervals and transported through a pumping system to the cuvette or sample vial of analytical equipment. The analytical equipment determines drug concentration and other properties. The dissolution profile for the dosage under evaluation—i.e., the percentage of drug dissolved in the test media at a certain point in time or over a certain period of time—can be calculated from the measurement of analyte concentration in the sample taken. The types of analytical equipment commonly provided include those adapted for effecting analytical techniques such as high-performance liquid chromatography (HPLC) and spectral analysis. HPLC entails separating the chemical compounds of the sample for discrete analysis by a detection device (which may be a simply designed UV spectrometer). Flow cells can be used in conjunction with HPLC as shown, for example, in U.S. Pat. No. 4,886,356 wherein Z-type flow cells are disclosed. As one example for implementing spectral analysis, a spectrophotometer uses ultraviolet (UV) and/or visible light to scan the sample and calculate light absorbance values. In one specific method involving the UV or UV-vis spectrophotometer, the UV sipper method, the sample is transferred to a flow cell contained within the spectrophotometer, is scanned while residing in the flow cell, and is then returned to the test vessel. The sample return step is advantageous in that it significantly reduces any analytical errors potentially resulting from a volumetric reduction in the solution still being developed in the test vessel. In general, spectrophotometric techniques are considered to be easier to implement than HPLC techniques for many applications.

The concentration of a given analyte in a sample through spectrochemical determination typically involves several steps. These steps can include (1) acquiring an initial sample (e.g., providing a dissolution testing apparatus with a dosage form such as a drug tablet that has been manufactured from a bulk material, or conducting chromatography, dialysis, and so on); (2) performing sample preparation and/or treatment to produce the analytical sample (e.g., dissolving the dosage from in dissolution media, and possibly adding reagents or pH factor-modifying agents, thereby creating a formulation suitable for measurement or detection by certain instruments); (3) using a sample introduction system to present the analytical sample to the sample holding portion of a selected analytical instrument (e.g., transferring the sample to the sample-holding portion of a UV spectrophotometer); (4) measuring an analytical signal (e.g., an optical signal) derived from the analytical sample; (5) establishing a calibration function through the use of standards and calculations; (6) interpreting the analytical signal; and (7) feeding the interpreted signal to a readout and/or recording system.

Conventional equipment employed in carrying out the above processes are generally known in various forms. Measurement of the analytical signal involves employing a suitable spectrochemical encoding system to encode the chemical information associated with the sample, such as concentration, in the form of an optical signal. In spectrochemical systems, the encoding process entails passing a beam of light through the sample under controlled conditions, in which case the desired chemical information is encoded as the magnitude of optical signals at particular wavelengths. Measurement and encoding can occur in sample cells, cuvettes, flow cells, and other sample containers of various designs. Flow cells permit increased sample throughput and facilitate the automation of filling and cleaning procedures. Test media and calibration media can be pumped or otherwise transferred into the flow cell, and the flow stopped for conducting an absorption measurement. After the measurement is taken, the pumping rate can be adjusted, and the liquid flow adjusted or reversed as needed, so as to remove the entire sample from the flow cell. The flow cell and associated liquid conduits can then be rinsed and another sample introduced into the flow cell. Flow cells can also be utilized to take absorption measurements on flowing streams of analyte-containing media, thereby making the measurement or analysis time-dependent. In this latter case, the flow rate and data acquisition time are controlled to ensure that the absorbance value is obtained for the sample at the proper time.

In addition, a suitable optical information selector must be used to sort out or discriminate the desired optical signal from the several potentially interfering signals produced by the encoding process. For instance, a wavelength selector can be used to discriminate on the basis of wavelength, or optical frequency. A radiation transducer or photodetector is then activated to convert the optical signal into a corresponding electrical signal suitable for processing by the electronic circuitry normally integrated into the analytical equipment. A readout device provides human-readable numerical data, the values of which are proportional to the processed electrical signals.

Considering all of the physical events that must occur over the course of sample preparation and analysis, adequate procedures for calibration or standardization of the system are usually required. For example, standards of known concentration can be introduced at one or more points along the liquid flow circuit of the system. Calibration data can thus be generated, stored and used as part of the analyzing process. Modern calibration procedures are often controlled by computer software. Indeed, a computer-controlled system can be provided to interface with many of the various components of the sample preparation and analysis systems. Such programmable systems are useful for monitoring and coordinating the various hardware operations, as well as for processing both the test data and the calibration data.

For spectrophotometers operating according to UV-vis molecular absorption methods, the quantity measured from a sample is the magnitude of the radiant power or flux supplied from a radiation source that is absorbed by the analyte species of the sample. Ideally, a value for the absorbance A can be validly calculated from Beer's law:

$$A = -\log T = -\log \frac{P}{P_0 = abc,}$$

where T is the transmittance, $P_0$ is the magnitude of the radiant power incident on the sample, P is the magnitude of the diminished (or attenuated) radiant power transmitted from the sample, a is the absorptivity, b is the pathlength of absorption, and c is the concentration of the absorbing species.

It thus can be seen that under suitable conditions, absorbance is directly proportional to analyte concentration through Beer's law. The concentration of the analyte can be determined from the absorbance value, which in turn is calculated from the ratio of measured radiation transmitted and measured radiation incident. In addition, a true absorbance value can be obtained by measuring a reference or blank sample and taking the ratio of the radiant power transmitted through the analyte sample to that transmitted through the blank sample.

Ordinarily, the sample is transferred to a sample cell that is contained within the analytical instrument (e.g., spectrophotometer) itself. An example of a conventional dissolution testing system is disclosed in U.S. Pat. No. 6,060,024. Samples are taken from test vessels and, using sampling pumps, carried over sampling lines and through sampling filters. The samples are then transported either to a UV analyzer containing six cells, to an HPLC system, or to a fraction collector.

U.S. Pat. No. 6,002,477, commonly assigned to the owner of the present application, discloses a spectrophotometer that contains a sample cell and a reference cell. A pulsed light source such as xenon flash tube emits very short, intense bursts of light that, after possibly being redirected by one or more reflective surfaces, passes through the entrance slit of a monochromator. After encountering one or more other reflective surfaces, gratings, and apertures or slits, the incident light beam is divided by a fixed beam splitter into two beams having a predetermined intensity ratio. One of these beams passes through the reference cell, and the beam transmitted from the reference cell is received by a reference detector. The other beam passes through the sample cell, and the beam transmitted from the sample cell is received by a sample detector. Provision is also made for measuring the dark signal, which is a measurement of the signal when no light from the light source reaches a detector. The sample, reference, and dark measurements are used to accurately calculate the absorbance of the sample. In another embodiment, the pulsing of the light source is synchronized by control means with the rotation of a carousel. The carousel holds several sample cuvettes, such that its rotation brings each cuvette into position at the sample cell in a step-wise manner.

Other examples of UV-vis spectrophotometers are those available from Varian, Inc., Palo Alto, Calif., and designated as the CARY™ Series systems. In particular, the Varian CARY 50™ spectrophotometer includes a sample compartment that contains a sample cell through which a light beam or pulse passes. Several sizes of sample cells are available. In addition, the spectrophotometer can be equipped with a multi-cell holder that accommodates up to eighteen cells. A built-in movement mechanism moves the cells past the light beam.

U.S. Pat. No. 4,279,860 discloses a multiple injector flow-through dissolution cell designed to handle dosages that have very high dissolution rates. A plurality of flow channels can selectively provide different specimens for the dissolution cell. The dissolution cell itself includes a mixing paddle, and thus functions as the test vessel for the dissolution system. A sample from the dissolution cell is sent through an output line to a spectrophotometer for both measurement and analysis. Fiber-optics are not employed at the dissolution cell.

U.S. Pat. No. 4,431,307 discloses a cuvette-set matrix containing an array of cuvettes adapted for use in measurements using light beams. Each cuvette is provided with a bottom optical window. All other portions of each cuvette are impervious to light in order to prevent the radiation directed into a particular cuvette from disturbing measurements taken in adjoining cuvettes. The cuvette-set matrix is adapted to receive a matrix of measurement beams containing a plurality of sources of measurement beams, such that one source of measurement beams is associated with each cuvette. A detector matrix is disposed on the side of the cuvettes opposite to the side at which the matrix of measurement beams is disposed. Thus, for each cuvette, the measurement beam emitted from the source passes through the liquid contained in the cuvette, through the optical window of the cuvette, and into the detector associated with the cuvette.

Ordinarily, the sample is transferred to a sample cell that is contained within the analytical instrument (e.g., spectrophotometer) itself. In other recently developed systems, fiber-optics are being used in conjunction with UV scans to conduct in-situ absorption measurements—that is, measurements taken directly in the sample vessels of either dissolution test equipment or sample analysis equipment. Fiber optic cables consist of, for example, glass fibers coaxially surrounded by protective sheathing or cladding, and are capable of carrying monochromatic light signals. There have been some applications of fiber-optics in the pharmacological testing industry. In particular, some fiber-optic sampling techniques have been employed as part of dissolution testing. In conventional fiber-optic techniques, a fiber-optic probe is placed directly into the dissolution media and hence its method is described as "in-situ". Unfortunately, particulates in the media tend to interfere with the UV scan and consequently produce inaccurate data. Appropriate software programs can be used to compensate for the inconsistencies caused by the particulates. However, because each drug sample (e.g., tablet) has unique particulate features, every sample being tested requires a separate algorithm for correcting the errors caused by the particulates of the tablet. Moreover, fiber-optic probes induce turbulence in the dissolution media. Current fiber-optic techniques are also disadvantageous in that they require calibration prior to each test run. First, "standard" media must be put into a test tube and placed over the fiber-optic probe. Second, "blank" media" must be put into a test tube and placed over the fiber-optic probe. The test is then initiated and the UV data are acquired.

One recent example of an in-situ fiber-optic method associated with dissolution testing is disclosed in U.S. Pat. No. 6,174,497. This method involves submerging a dip-type fiber-optic UV probe in test media contained in a dissolution vessel, and keeping the probe submerged over the course of the dissolution run. Several probes can be operatively associated with a corresponding number of test vessels, with each probe communicating with its own UV spectrometer. The probe can be disposed within the shaft of an agitation device in order to reduce effects related to flow aberration, since only the mixing shaft/dip probe combination resides in the test vessel. A light beam (UV radiation) provided by a deuterium lamp is directed through fiber-optic cabling to the probe. Within the probe, the light travels through a quartz lens seated directly above a flow cell-type structure, the interior of which is filled with a quantity of the test media. The light passes through the test media in the flow cell, is reflected off a mirror positioned at the terminal end of the probe, passes back through the flow cell and the quartz lens, and travels through a second fiber-optic cable to a spectrometer. Thus, only the light beam, and not the sample, is removed from the test vessel during the procedure.

The probe disclosed in U.S. Pat. No. 6,174,497 is intended to reduce analytical errors and noise sources associated with conventional techniques requiring the removal of media from the test vessel. Such analytical errors can result from operator errors, programming errors, equipment malfunctions, contamination, clogging, media loss, and so on. This arrangement, nevertheless, requires the use of software algorithms to correct for noise-related physical events. Moreover, the fact that the probe is constantly submerged means that hydrodynamic influences can still affect the release rate of the dosage formulation being tested. While the position of the probe within the test vessel could be controlled by a sampling manifold, providers of this particular design recommend that the probe be maintained in at least a partially submerged position to eliminate the occurrence of air bubbles and fouling due to drying. Furthermore, the fact that the probe remains immersed within the contents of the test vessel means that analytical errors can result from the interference of particulates in the media being detected by the probe, as there is no provision for filtering such particulates from the media.

Another recent example of an in-situ fiber-optic method associated with dissolution testing, available from LEAP Technologies, Inc., utilizes a U-shaped dip probe that is inserted into a test vessel. One leg of the U-shaped probe contains a source optical fiber and the other leg contains the return optical fiber. A gap between the ends of the fibers is defined at the base of the U-shape, across which the light beam is transmitted through the media of the test vessel.

U.S. Pat. No. 5,005,005 also discloses a U-shaped optical-based sensor. The sensor is constructed by forming a U-shaped loop section in a single fiber-optic cable, retaining the shape of the loop in a support structure, and removing the sheathing and coating materials of a section of the cable corresponding to the curved section of the U-shape. This removal creates an exposed fiber core section through which light can be transferred. One end of the cable communicates with a light source while the other end communicates with a photodiode. Ice detection, soil moisture detection, underground tank leak detection, and fluid level sensing are disclosed as applications of the sensor.

For the previously described Varian CARY 50™ spectrophotometer, a fiber-optic dip probe coupler is available to enable in-situ sample measurement methods and effectively replace the need for a sipper accessory. This fiber optic coupler can be housed in the spectrophotometer unit in the place of the conventional sample cell. The coupler includes suitable connectors for coupling with the source and return optical fiber lines of a remote fiber-optic dip probe. The light beam from the light source of the spectrophotometer is directed to source line of the dip probe, and the resulting optical signal transmitted back to the spectrophotometer through the return line.

Fiber optics have also been employed in connection with sample-holding cells. For example, U.S. Pat. No. 6,069,694 discloses a flow cell having two fiber-optic cable assemblies that are spaced apart on opposite sides of the flow cell. Each cable assembly terminates at a distal end that requires the use of either a sapphire window or a lens. The path length between the distal ends is adjustable. The liquid to be analyzed flows through the flow cell between the opposing ends of the cable assemblies. The light passing through the flow cell is carried over one of the cable assemblies to an infrared analyzing instrument.

U.S. Pat. No. 5,715,173 discloses an optical system for measuring transmitted light in which both a sample flow cell and a reference flow cell are used. Light supplied from a light source is transmitted through a collimator lens to a pair of condenser lenses. One part of the light travels through an optical fiber to the sample flow cell, while the other part of the light travels through a second optical fiber to the reference flow cell. On the input side of each flow cell, the respective optical fiber terminates at a collimator lens. On the output side of each flow cell, light transmitted through the cell enters an optical fiber through a condenser lens. The path of transmitted light from each flow cell is directed toward an optical detector, and is controlled by an optical path switcher in the form of a light selecting shutter or disk.

Another example of an optical measurement device is disclosed in U.S. Pat. No. 5,077,481, in which the measurement device is inserted into the liquid sample cup of a spectrophotometer. The device is cylindrical and defines an internal cavity accessible by three lateral openings. Send and return optical fibers are situated above the cavity, and a concave reflection device is situated below the cavity. When inserted into the liquid sample cup, liquid contained in the cup is admitted into the cavity via the lateral openings. A light beam from one of the optical fibers passes twice through the liquid residing in the cavity, since it is reflected off the reflection component, and subsequently is transported away from the measurement device through the other optical fiber.

U.S. Pat. No. 5,428,696 discloses a fiber-optic sample analyzing system in which a plurality of cuvettes each have a source optical fiber and a return optical fiber, with the terminal ends of the fibers requiring the use of light-directing lenses. A device is provided for selecting a source fiber to receive passed radiation through a selected sample of one of the cuvettes, and for returning transmitted radiation from the selected cuvette through a selected return fiber to a spectrophotometer.

U.S. Pat. No. 4,528,159 discloses a sample analysis system in which a belt containing a series of disposable reaction cuvettes is driven along a track so as to guide the cuvettes through several analysis stations. A separate photodetector tube is required for each analysis station. Light guides are used to transmit light from a light source, through filter wheels, through the reaction compartments of the cuvettes, and to the photodetectors.

U.S. Pat. No. 5,804,453 discloses a system in which a fiber-optic biosensor probe is inserted into a test tube. The probe receives a light beam from a light source and sends a testing signal to the photodetectors of a spectrometer. Time division multiplexing and demultiplexing are implemented to distribute light to and from several biosensors. Switching among inputs and outputs is controlled by an input control signal provided by an electronic clocked counter.

U.S. Pat. No. 5,580,784 discloses a system in which a plurality of chemical sensors are associated with several sample vials and arranged between a light source and a photodetector. Optical fibers are used to direct radiation into each sensor, as well as to direct emissions out from the sensors. A wavelength-tunable filter is combined with an optical multiplexer to direct radiation serially to each sensor through the fibers.

In view of the current state of the art, it would be advantageous to provide improved flow cells and flow cell structures (or any other similar type of structure adapted for sample measurement) that are designed and arranged in a manner conducive to high-quality dissolution testing, and that cooperate with fiber-optic components. In operation, such flow cells would not be inserted into the vessels in which dissolution is effected. At the same time, however, the flow cells and their associated liquid flow and fiber-optic components would not detrimentally affect data acquisition, measurement and analysis. It would also be advantageous to provide a liquid flow system adapted for use in conjunction with the improved flow cells, and that would enable improved sampling and calibration procedures.

SUMMARY OF THE INVENTION

The present invention is adapted most advantageously for use in connection with the dissolution test vessels of dissolution media preparation/testing equipment and sample analyzing instruments. However, as the various features and functions of the invention are described herein, it will become evident that the invention finds utility in various sample measurement processes and thus is not restricted to dissolution-related processes. The invention provides remote, non-resident flow-through cells for the measurement of samples of media (e.g., dissolution media) taken from the test vessels. The media are removed from the dissolution vessel, preferably using a filter (for example, a 10-micron filter) and a pump, and then sent to the flow cell where the fiber optic probe or other type of fiber-optic device resides. The total distance from the sampling point to the flow cell and back to the dissolution vessel is very short, thereby negating any adverse effects from the use of liquid tubing. Moreover, the total dead volume while sampling—i.e., the volume of media residing in liquid tubing and thus not undergoing dissolution—is advantageously much less than in present sampling systems. The problems conventionally caused by particulates do not arise in the present invention, as the media is filtered prior to the fiber-optic sampling point. As a result, software-effected adjustments are not required, and all dosages can be tested without software modifications. The invention further provides an arrangement of liquid flow circuitry that enables calibration of all flow cells to be effected simultaneously and in an automated manner.

The invention in one aspect provides a sampling manifold comprising, for example, a sampling cannula, a return cannula, and a temperature-measuring probe for each test vessel. In use, the sample cannulas and temperature-measuring probes are placed inside the vessel only while a sample is being taken, and are absent from the dissolution media at all other times during testing. As a result, the detrimental effects caused by such probes, such as turbulence, are significantly reduced. The invention further provides flow control devices such as solenoid valves that simplify the calibration process. For example, in a system containing eight vessels of which six are used as test vessels, the two other vessels can be used to hold standard media and blank media, respectively. The system uses the appropriate media at the time the system is being calibrated, thereby eliminating any user intervention and also significantly reducing calibration time. All eight vessels can be calibrated at the same time with this system, unlike the existing method that requires each vessel to be manually calibrated one vessel at a time with the use of a test tube.

According to one embodiment of the present invention, a manifold device is provided for use in sample measurements. The manifold device comprises a manifold body defining a plurality of flow cells therein, a plurality of liquid input lines and liquid output lines, and a plurality of probes. Each liquid input line and output line fluidly communicates with a corresponding one of the flow cells, providing a liquid flow path through the corresponding flow cell. The probes are at least partially disposed within the manifold body. Each probe comprises an optical fiber input line and an optic fiber output line. Each optical fiber input line and optical fiber output line communicate with a corresponding one of the flow cells.

According to another embodiment of the present invention, a manifold device for use in sample measurements comprises a manifold body, a plurality of flow cells disposed within the body, a plurality of liquid input lines and output lines, and a plurality of optical fiber input and output lines. The liquid input and output lines and the optical fiber input and output lines each communicate with a corresponding one of the flow cells. Each corresponding liquid input line and liquid output line provides a liquid flow path through the corresponding flow cell. Each optical fiber output line is disposed in opposing, optically-aligned relation to the corresponding optical fiber input line associated with one of the flow cells. Each corresponding optical fiber input line and optical fiber output line provide an optical path through the corresponding flow cell generally transverse to the liquid flow path.

According to yet another embodiment of the present invention, a dissolution media sampling system comprises a plurality of test vessels, a plurality of test media sampling lines, a plurality of test media return lines, and a plurality of remote flow cells. Each test media sampling line is adapted for transferring a quantity of test media from a corresponding one of the test vessels. Each test media return line adapted for transferring the quantity of test media back to the corresponding test vessel. Each flow cell fluidly communicates with a corresponding one of the test media sampling lines and test media return lines, and each flow cell communicates with an optical fiber input line and an optical fiber output line.

According to still another embodiment of the present invention, the sampling system includes a distributing mechanism or system for distributing one or more types of calibration media, such as blank media or standard media, to the flow cells. In one specific embodiment, the distributing mechanism comprises a plurality of first valves and a plurality of second valves, each first valve selectively establishing a first input flow path from a first calibration vessel to one of the flow cells, and each second valve selectively establishing a first output flow path from the flow cell to the first calibration vessel.

According to a further embodiment of the present invention, a dissolution media preparation and/or testing apparatus is provided. The apparatus comprises a structural frame, a vessel plate supported by the frame and having a plurality of vessel-holding apertures adapted for supporting a plurality of vessels, and a plurality of flow cells supported by the frame and disposed in remote relation to the vessel-holding apertures. The apparatus further comprises a plurality of liquid input lines and liquid output lines. Each liquid input line is operatively associated with a corresponding one of the vessel-holding apertures and communicates with a corresponding one of the flow cells. Each liquid output line is operatively associated with a corresponding one of the vessel-holding apertures and communicates with a corresponding one of the flow cells. The apparatus also comprises a plurality of optical fiber input lines and optical fiber output lines. Each optical fiber input line and corresponding optical fiber output line communicates with a corresponding one of the flow cells. In one specific embodiment of the apparatus, an automated assembly is supported by the frame and is movable to insert a distal portion of at least one of the liquid input lines through a corresponding one of the vessel-holding apertures.

According to a still further embodiment of the present invention, a dissolution system comprises a vessel plate supporting a plurality of test vessels, a remote manifold device defining a plurality of flow cells, and a sample analyzing system. Also provided are a plurality of test media sampling lines and test media return lines. Each test media sampling line is adapted for transferring a quantity of test media from a corresponding one of the test vessels to a corresponding one of the flow cells. Each test media return line is adapted for transferring the quantity of test media from the corresponding flow cell back to the corresponding test vessel. A plurality of optical fiber input lines and output lines are also provided. Each optical fiber input line communicates with a corresponding one of the flow cells, and each corresponding optical fiber output line communicates with the corresponding flow cell. The sample analyzing system communicates with at least one of the flow cells through a corresponding pair of optical fiber input and output lines.

According to an additional aspect of the present invention, a method is provided for measuring an analyte that is dissolving or has dissolved in test media. In the method, a sample of analyte-containing test media is transferred from a container into a remote flow cell. Light radiation of a first intensity is transmitted from a source optical fiber into the flow cell, wherein a portion of the light radiation is absorbed by analytes in the sample. Light radiation of a second intensity lower than the first intensity is transmitted from the flow cell, through a return optical fiber, and to a sample analyzing apparatus. The sample is returned to the container at some point in time during or after the sample is subjected to the light radiation in the flow cell. At further time intervals, which may correspond to further degrees of dissolution of the analytes in the media held in the container, additional samples can be drawn from the container and introduced into the same flow cell, and additional measurements taken via further transmissions of electromagnetic energy through the flow cell. Also, several remote flow cells can be provided so that multiple samples from different containers can be measured and analyzed simultaneously or according to a predetermined sequence. In this latter case, it is advantageous to utilize a remote flow cell manifold device as provided according to other embodiments described herein.

According to another method of the present invention, calibration procedures can be performed using the same remote flow cells used for measuring the analytes under investigation. Arrangements of the sampling systems and liquid flow circuits described herein can be employed for this purpose.

DETAILED DESCRIPTION OF THE INVENTION

In general, the term "communicate" (e.g., a first component "communicates with" or "is in communication with" a second component) is used herein to indicate a structural, functional, mechanical, optical, or fluidic relationship between two or more components or elements. As such, the fact that one component is said to communicate with a second component is not intended to exclude the possibility that additional components may be present between, and/or operatively associated or engaged with, the first and second components.

As used herein, the terms "beam," "pulse," and "optical signal" are intended to be interchangeable to indicate that the present invention is applicable to the transmission of light energy by both continuous and non-continuous methods.

Figure 1:
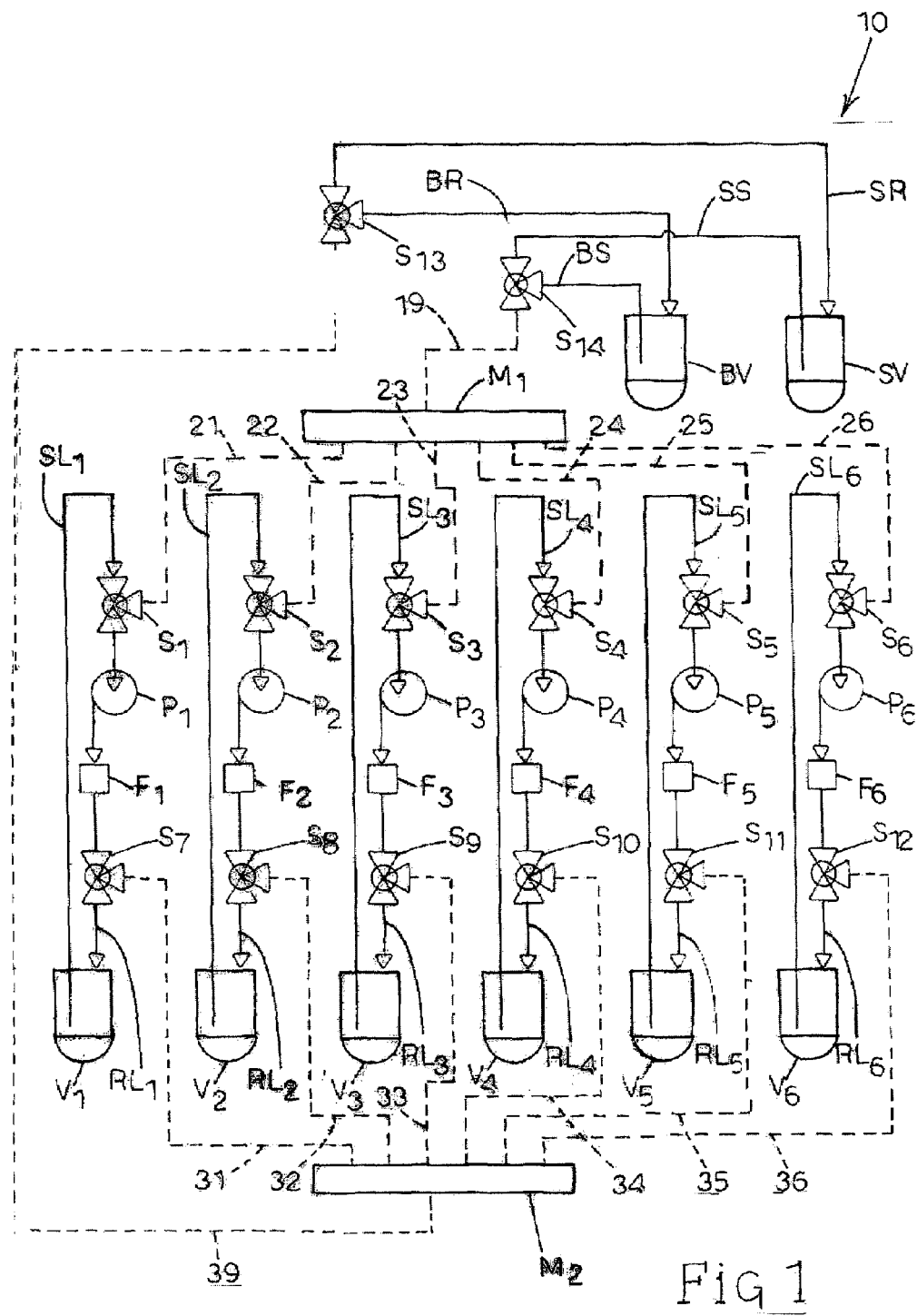
FIG. 1 is a schematic diagram of a liquid flow system adapted for use in a dissolution testing system in accordance with the present invention.
Figure 2:
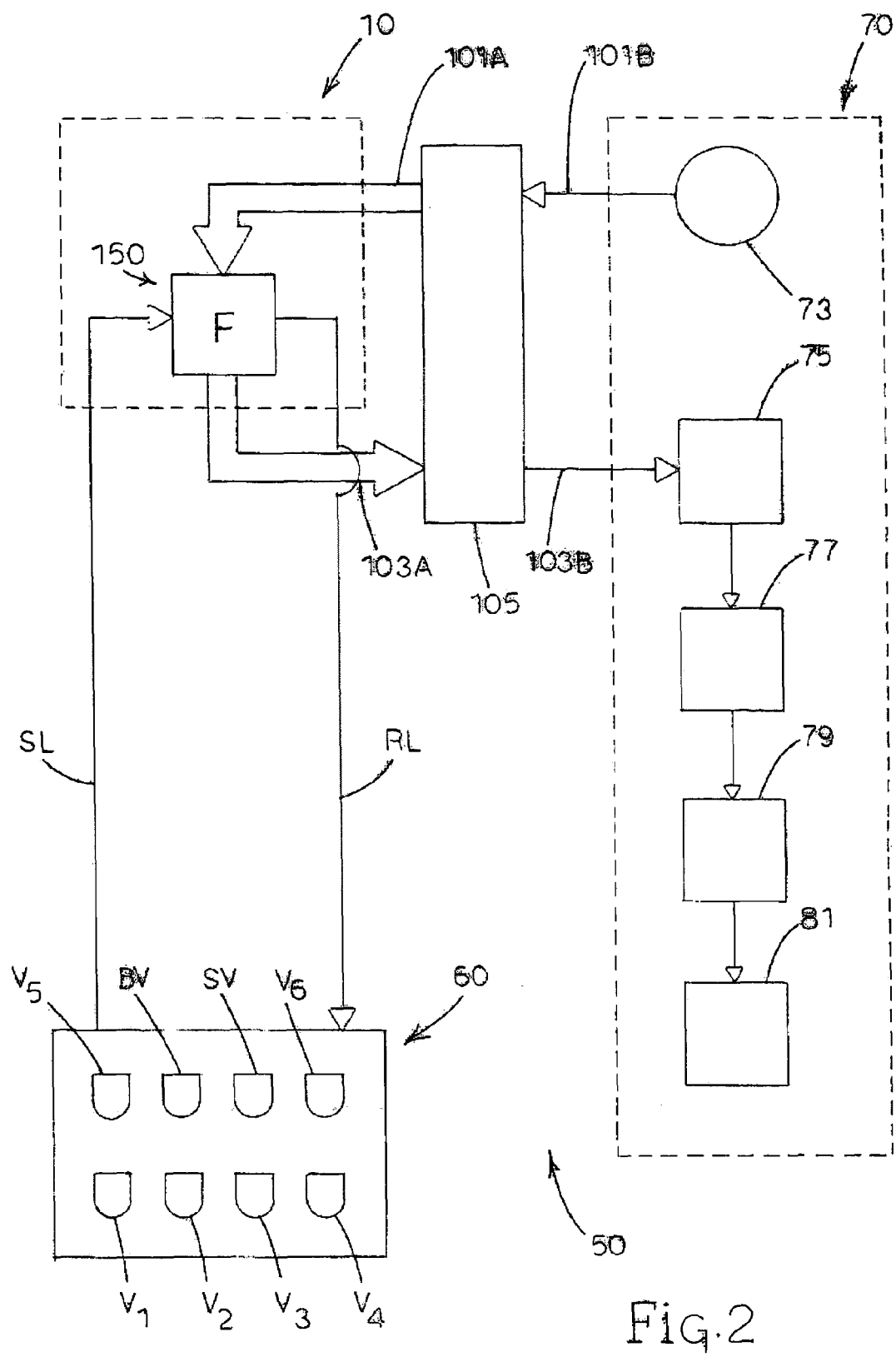
FIG. 2 is a schematic diagram of a dissolution testing system provided according to the present invention.

Referring now to FIG. 1, a dissolution media sampling system, generally designated 10, is illustrated in accordance with the present invention. Sampling system 10 includes a plurality of (e.g., six) test vessels $V_1$-$V_6$, a blank vessel BV, and a standard vessel SV. Test vessels $V_1$-$V_6$ are used to hold liquid media that contain the components of, for example, a dissolved pharmaceutical drug product, such as therapeutically active particles (i.e., the analytes of interest) and excipients. Blank vessel BV is used to hold blank media, which does not contain any analytes. Standard vessel SV is used to hold the standard media, which contains a reference substance having one or more known properties such as analyte concentration. The specific property of the reference substance that should be known will depend on the type of equipment or instrumentation used to analyze samples taken from test vessels $V_1$-$V_6$. For the purpose of describing the present exemplary embodiment, a sample analyzing apparatus, generally designated 70 in FIG. 2, is provided in the form of a UV or UV-vis spectrophotometer. The invention, however, is not limited to any specific type of optical measurement or sample analyzing apparatus, nor to any specific design of spectrophotometer if such instrument is used. Possible configurations for the spectrophotometer include those that utilize single detectors or multi-channel detectors, those that are adapted to perform single-beam or double-beam measurements, those that are adapted to perform horizontal-beam or vertical-beam measurements, and those that can perform measurements of fixed wavelength or of the entire absorption spectra for the analyte. Moreover, for the purpose of the present disclosure, the term "sample analyzing system" is intended to encompass any analyzing equipment compatible with the systems and methods described herein. Such equipment may include, but is not limited to, HPLC, spectrometers, photometers, spectrophotometers, spectrographs, and similarly termed equipment.

Test vessels $V_1$-$V_6$, blank vessel BV, and standard vessel SV can all be mounted in an array on a vessel plate or other mounting means that is integrated with a dissolution media preparation apparatus, generally designated 60 in FIG. 2. Dissolution media preparation/testing apparatus 60 can be automated or semi-automated. An example of a dissolution media preparation apparatus 60 is described in more detail hereinbelow with reference to FIG. 6.

In accordance with the present invention, media sampling system 10 includes a plurality of flow cells $F_1$-$F_6$. Through suitable media input and output connections, each flow cell $F_1$-$F_6$ is adapted to permit the flow of analyte-containing media through an internal detection area defined by the structure of flow cell $F_1$-$F_6$. In addition, fiber-optic components comprising optical fiber cores are associated with each flow cell $F_1$-$F_6$. Embodiments of the fiber-optic components are not specifically shown in FIG. 1, but are described hereinbelow with reference to FIGS. 3-5C. Each flow cell $F_1$-$F_6$ and its corresponding fiber-optic components cooperatively enable an analytical signal to be generated within flow cell $F_1$-$F_6$ and transmitted to sample analyzing apparatus 70 for determination of the absorbance value of the sampled analytes. In the embodiment illustrated in FIG. 1, one flow cell $F_1$-$F_6$ is associated with each corresponding test vessel $V_1$-$V_6$. Each flow cell $F_1$-$F_6$ is "remote" or free-standing, meaning that each flow cell $F_1$-$F_6$ is situated remotely in relation to its corresponding test vessel $V_1$-$V_6$. Preferably, each flow cell $F_1$-$F_6$ is also situated remotely in relation to (and thus not integrated with) any sample analyzing system 70 provided. Moreover, flow cells $F_1$-$F_6$ can be advantageously integrated into a unitary flow cell manifold block as described in more detail hereinbelow. In such an embodiment, the manifold block can also be described as being remote or free-standing. Finally, according to an aspect of the invention, whether or not flow cells $F_1$-$F_6$ are integrated into a manifold block, flow cells $F_1$-$F_6$ can nevertheless be mounted to the frame or structure of dissolution media preparation apparatus 60. This latter feature enables the respective lengths of the various liquid lines associated with flow cells $F_1$-$F_6$ to be significantly reduced, which in turn reduces any signal noise or other deleterious effects caused by the circulation of samples in and out of test vessels $V_1$-$V_6$. At the same time, however, neither flow cells $F_1$-$F_6$ nor any type of fiber-optic probe reside in vessels $V_1$-$V_6$ during dissolution, sampling and measurement, so that the quality of the dissolution data remains high.

In further accordance with the present invention, media sampling system 10 includes a plurality of liquid flow path-directing, three-way solenoid valves $S_1$-$S_{14}$, liquid pumps $P_1$-$P_6$, liquid sampling lines $SL_1$-$SL_6$, and liquid return lines $RL_1$-$RL_6$ (as well as other appropriate liquid conduits interconnecting these various components). All of these components are arranged with flow cells $F_1$-$F_6$ and test vessels $V_1$-$V_6$ to define a plurality of liquid sampling circuits, such that one liquid sampling circuit is associated with each flow cell $F_1$-$F_6$ and accompanying test vessel $V_1$-$V_6$. For example, test vessel $V_1$ is part of the sampling circuit containing sampling line $SL_1$, valve $S_1$, pump $P_1$, flow cell $F_1$, valve $S_7$, and return line $RL_1$. The term "sampling line" (and likewise "return line") can encompass a cannula or other probe-type element adapted for insertion into a test vessel, as well as the liquid conduit or conduits to which the cannula is connected to enable transfer of liquid media to or from an associated test vessel. Each sample cannula and return cannula, respectively associated with each sampling line $SL_1$-$SL_6$ and return line $RL_1$-$RL_6$, can be supported by a movable (manually, or through automated or semi-automated means) head or manifold assembly forming a part of dissolution media preparation apparatus 60 or other liquid handling apparatus. The several pumps $P_1$-$P_6$ depicted in FIG. 1 can be integrated into a commercially available, multi-channel pump unit such as the peristaltic type. In addition, each sampling line $SL_1$-$SL_6$ includes a filter of an appropriate mesh size (e.g., ten microns) that is situated at some point upstream of its corresponding flow cell $F_1$-$F_6$. For example, the filter can be provided at the tip of a sampling cannula that is inserted into test vessel $V_1$-$V_6$. Because the sample is filtered upstream of the fiber-optic sampling point in flow cell $F_1$-$F_6$, problems conventionally associated with the presence of particulates at the sampling point are not encountered. Accordingly, software-implemented adjustments are not needed.

A typical sampling operation can be described with reference to the sampling circuit corresponding to test vessel $V_1$ in FIG. 1, with the understanding that similar operations can be carried out along the other sampling circuits associated with test vessels $V_2$-$V_6$, either simultaneously or according to a predetermined sequence. Using dissolution media preparation apparatus 60 in FIG. 2 as an example, the dissolution media in test vessel $V_1$ is first prepared according to known procedures by dissolving a drug product provided in a dosage form such as a tablet in a solvent provided in test vessel $V_1$. At one or more predetermined time intervals, valves $S_1$ and $S_7$ are switched to establish flow in the direction leading into flow cell $F_1$ and back into test vessel $V_1$. A predetermined aliquot of analyte-containing dissolution media (i.e., a sample) is drawn from test vessel $V_1$ into sampling line $SL_1$, such as by using a sampling cannula that is lowered into test vessel $V_1$, and the sample is transferred through valve $S_1$ into flow cell $F_1$ under the influence of pump $P_1$.

As described in reference to FIG. 2 hereinbelow, a beam of electromagnetic energy such as UV light is passed through flow cell $F_1$, with the direction of light ordinarily being transverse to the direction of liquid flow. The analytical signal resulting from the passage of light energy through flow cell $F_1$ is sent to sample analyzing apparatus 70 (see FIG. 2) for processing. The sample is then quickly returned to test vessel $V_1$ from flow cell $F_1$ through valve $S_7$. As an alternative to holding the sample in flow cell $F_1$ during the measurement and afterwards re-establishing flow, analyte-containing media can be continuously circulated through in flow cell $F_1$ and measurements taken at predetermined time intervals. In either case, by recycling media back into vessels $V_1$-$V_6$, the respective media volumes of test vessels $V_1$-$V_6$ are not reduced as a consequence of the test runs. Thus, there is little or no risk of precipitation of the analytes from the media. Moreover, since one flow cell $F_1$-$F_6$ is provided for each corresponding test vessel $V_1$-$V_6$, there is no risk of cross contamination between samples. Additionally, samples in each flow cell $F_1$-$F_6$ can be measured simultaneously, making the invention compatible for handling very fast dissolving samples. With respect to one or more of flow cells $F_1$-$F_6$, these procedures can be repeated over a succession of time intervals in order to obtain several data points, such as when generating a dissolution profile for one or more particular samples.

Referring again to FIG. 1, media sampling system 10 further includes a calibration system comprising blank vessel BV, standard vessel SV, one or more liquid flow path-directing manifold units $M_1$ and $M_2$, additional three-way solenoid valves $S_{13}$ and $S_{14}$, and suitably connected additional liquid lines. Blank vessel BV and standard vessel SV can also be mounted in the vessel plate of dissolution media preparation/testing apparatus 60. In accordance with the present invention, the components of the calibration system are arranged such that each flow cell $F_1$-$F_6$ can be calibrated simultaneously without any human intervention, thereby significantly reducing calibration time. Media from blank vessel BV and/or standard vessel SV can be sent through flow cells $F_1$-$F_6$, and light beams passed through flow cells $F_1$-$F_6$. The optical signals generated in this manner can be processed and recorded by sample analyzing apparatus 70 in accordance with known calibration procedures. For instance, the light absorbance values obtained from analyzing a sample of the blank media can be subtracted from the light absorbance values obtained from analyzing a sample of the standard media. Reference values calculated in this manner can be compared with known data for the analytes contained in standard vessel SV, and adjustments to flow cells $F_1$-$F_6$ or sample analyzing apparatus 70 can be made or calibration curves generated as needed. Blank vessel BV or standard vessel SV could also be used to contain a rinsing fluid, if a separate rinse station is not otherwise provided in communication with media sampling system 10 or media preparation/testing apparatus 60.

To send blank media through flow cells $F_1$-$F_6$, valve $S_{14}$ is switched to establish flow from blank vessel BV to manifold unit $M_1$. Blank media is drawn from blank vessel BV into a blank media sampling line BS and transferred through valve $S_{14}$, through a manifold input line 19, and into manifold unit $M_1$. Valves $S_1$-$S_6$ are switched to establish flow from manifold unit $M_1$ through a plurality of manifold output lines 21-26 into each corresponding flow cell $F_1$-$F_6$. The blank media flows from manifold unit $M_1$ into each flow cell $F_1$-$F_6$ under the influence of each corresponding pump $P_1$-$P_6$, and light energy is passed through each flow cell $F_j$-$F_6$ to generate optical signals as previously described. Valves $S_7$-$S_{12}$ are switched to a position that directs the blank media from flow cells $F_1$-$F_6$ through respective bypass lines 31-36 to manifold unit $M_2$. Valve $S_{13}$ is switched to enable the transfer of the blank media from manifold unit $M_2$, through a single manifold output line 39, through valve $S_{13}$, through a blank media return line BR, and back into blank vessel BV.

To send standard media through flow cells $F_1$-$F_6$, an analogous procedure is followed. Valve $S_{14}$ is switched to establish flow from standard vessel SV to manifold unit $M_1$. Standard media is drawn from standard vessel SV into a standard media sampling line SS and transferred through valve $S_{14}$, through manifold input line 19, and into manifold unit $M_1$. Valves $S_1$-$S_6$ are switched to establish flow from manifold unit $M_1$ through manifold output lines 21-26 into each corresponding flow cell $F_1$-$F_6$. The standard media flows from manifold unit $M_1$ into each flow cell $F_1$-$F_6$ under the influence of each corresponding pump $P_1$-$P_6$, and light energy is passed through each flow cell $F_1$-$F_6$ to generate analytical signals. Valves $S_7$-$S_{12}$ are switched to a position that directs the standard media from flow cells $F_1$-$F_6$ through respective bypass lines 31-36 to manifold unit $M_1$. Valve $S_{13}$ is switched to enable the transfer of the standard media from manifold unit $M_2$, through manifold output line 35, through valve $S_{13}$, through a standard media return line SR, and back into standard vessel SV.

It will be understood that one or more rinsing, washing or back flushing steps can be performed if necessary as part of the testing and/or calibration procedures described herein. Either blank vessel BV or standard vessel SV could be used to hold, for example, a rinsing solvent. Alternatively, a solvent bottle or rinsing station, which may be integrated with media preparation/testing apparatus 60, could be used.

Referring to FIG. 2, basic components of a dissolution system, generally designated 50, are illustrated according to the present invention. Dissolution system 50 comprises media sampling system 10, media preparation/testing apparatus 60, and sample analyzing apparatus 70. Media sampling system 10 includes a set F of flow cells $F_1$-$F_6$ that can be integrated into a single manifold block generally designated 150 (which, in the present example, would be a six-input manifold block). Flow cell manifold block 150 can be designed according to any of the embodiments described in more detail hereinbelow. The various components comprising sample analyzing apparatus 70 will depend on the type of analytical signal to be measured and detected. If the desired analytical signal is the intensity of light radiation absorbed by analytes in each flow cell $F_1$-$F_6$, then sample analyzing system 70 can take the form of a UV spectrophotometer. In the case of a spectrophotometer, sample analyzing system 70 typically includes a stable, continuous source 73 of UV radiation such as a deuterium lamp or xenon arc lamp, a wavelength selector 75 or similar device, a radiation detector 77 such as a photoelectric detector or transducer, a signal processor 79, and a readout device 81. Because they function as transparent containers that hold the samples, flow cells F could also be considered to form a part of sample analyzing system 70.

In operation, one or more samples of dissolution media are transferred from selected test vessels $V_1$-$V_6$ (mounted, for example, in media preparation/testing apparatus 60) through dissolution media sample lines (collectively designated SL in FIG. 2) to corresponding flow cells F of manifold block 150, and subsequently returned to test vessels $V_1$-$V_6$ through dissolution media return lines (collectively designated RL in FIG. 2). Calibration operations can also be carried out using blank vessel BV and standard vessel SV as described previously. UV radiation source 73 sends a beam of light of intensity $P_0$ through a sheathed fiber optic input cable 101A, 101B into one or more selected flow cells F of manifold block 150. UV radiation source 73 and the sample residing in each flow cell F can together be considered as a signal generator, in that UV radiation source 73 and the sample conjoin to generate the analytical signal in the form of an attenuated beam of light of intensity P as the beam of light passes through the sample. The analytical signal is sent through a sheathed fiber optic output cable 103A, 103B to sample analyzing system 70 for detection and processing, and the concentration of the measured sample is determined from the value obtained for its measured light absorbance, using calibration curves if necessary. In the present example, in which sample analyzing system 70 is connected with a single light transmitting fiber-optic cable portion 101B and a single light receiving fiber-optic cable portion 103B, a multiplexer 105 or similar optical channel selection device can be employed. Accordingly, that portion of the input fiber-optic cable designated 101A represents a bundle of six fiber-optic input cables connected between multiplexer 105 and respective flow cells F, respectively, and that portion of the output fiber-optic cable designated 103A represents a bundle of six fiber-optic output cables connected between respective flow cells F and multiplexer 105.

Within sample analyzing system 70, wavelength selector 75 is typically provided in the form of a filter or monochromator that isolates a restricted region of the electromagnetic spectrum for subsequent processing. Detector 77 converts the radiant energy of the analytical signal into an electrical signal suitable for use by signal processor 79. Signal processor 79 can be adapted to modify the transduced signal in a variety of ways as necessary for the operation of sample analyzing system 70 and the conversion to a readout signal. Functions performed by signal processor 79 can include amplification (i.e., multiplication of the signal by a constant greater than unity), logarithmic amplification, ratioing, attenuation (i.e., multiplication of the signal by a constant smaller than unity), integration, differentiation, addition, subtraction, exponential increase, conversion to AC, rectification to DC, comparison of the transduced signal with one from a standard source, and/or transformation of the electrical signal from a current to a voltage (or the converse of this operation). Finally, readout device 81 displays the transduced and processed signal, and can be a moving-coil meter, a strip-chart recorder, a digital display unit such as a digital voltmeter or CRT terminal, a printer, or a similarly related device.

Figure 3:
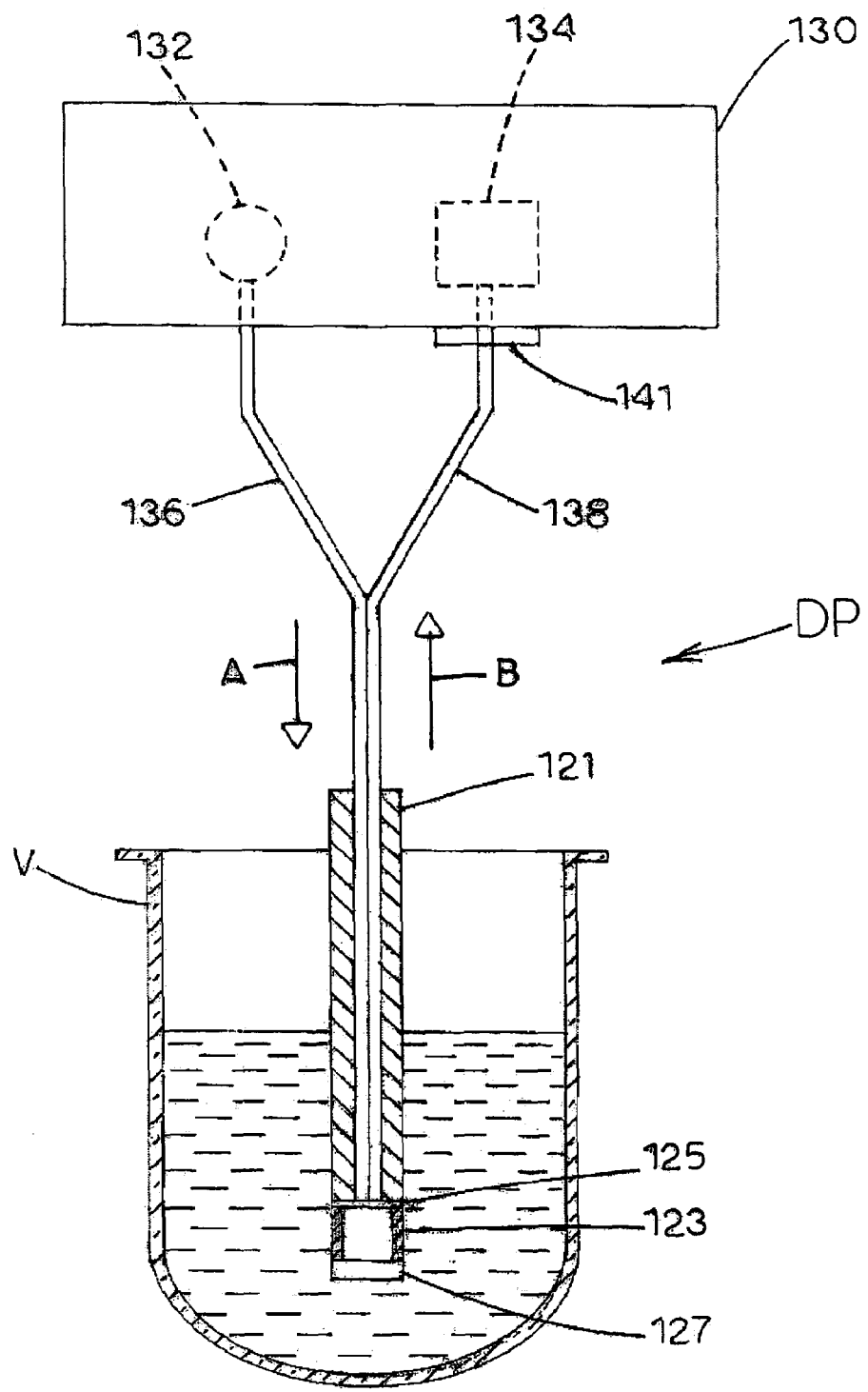
FIG. 3 is a partially cut-away, front elevation view of a conventional fiber-optic dip probe.

According to one embodiment of the invention, flow cell manifold block 150 (FIG. 2) is adapted to operatively receive a plurality of dip probes or fiber-optic probes of similar design. Referring now to FIG. 3, an example of a dip probe of conventional design, generally designated DP, is illustrated by way of background. In conventional use, dip probe DP is inserted into a test vessel V so that the lower portion of its tip 121 is submerged in media held by test vessel V, thereby allowing absorbance measurements directly in test vessel V. Dip probe DP typically includes a flow cell 123 or similar sample target area defined by a gap between a fused silica or quartz lens or seal 125 and a suitable light-reflective surface such as a mirror 127. Dip probe DP operates in conjunction with a spectrophotometer 130 that includes a light source 132 and a detection means such as a photodiode amplifier/detector 134. A first, light-transmitting fiber-optic cable 136 runs between spectrophotometer 130 and glass seal 125. A second, light-returning fiber-optic cable 138 runs between glass seal 125 back to spectrophotometer 130, and usually includes an interference filter 141 or similar component. In use, a beam of light emitted by light source 132 is guided by first fiber-optic cable 136 along the direction of arrow A into flow cell 123. This beam of light passes through the media residing in flow cell 123, is reflected by mirror 127, and thus is redirected into second fiber-optic cable 138 along the direction indicated by arrow B. The light beam then passes through interference filter 141 and returns to spectrophotometer 130 where the signal is processed by detector 134.

Figure 4A:
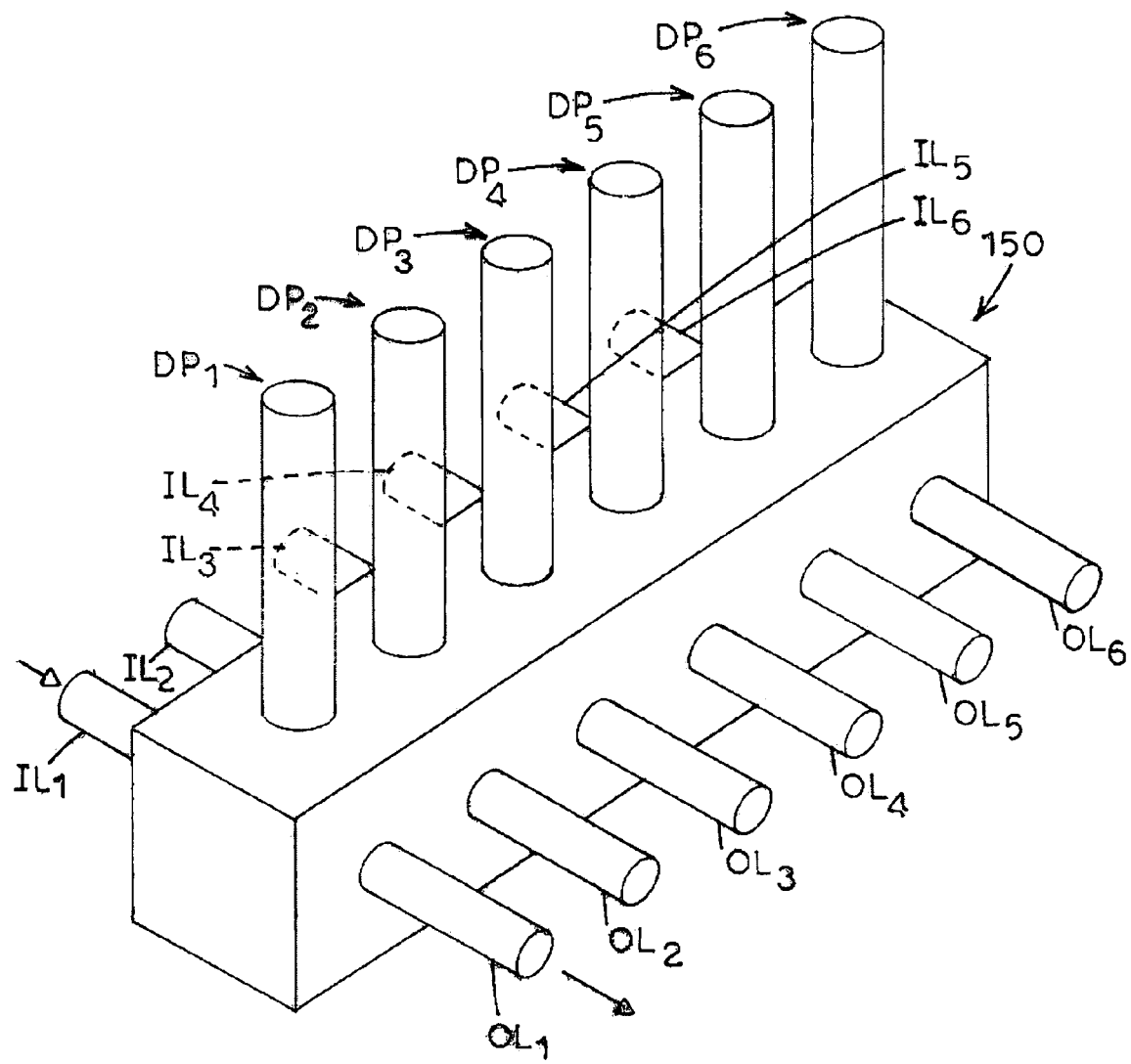
FIG. 4A is a perspective view of a flow cell manifold assembly provided according to one embodiment of the present invention.
Figure 4B:
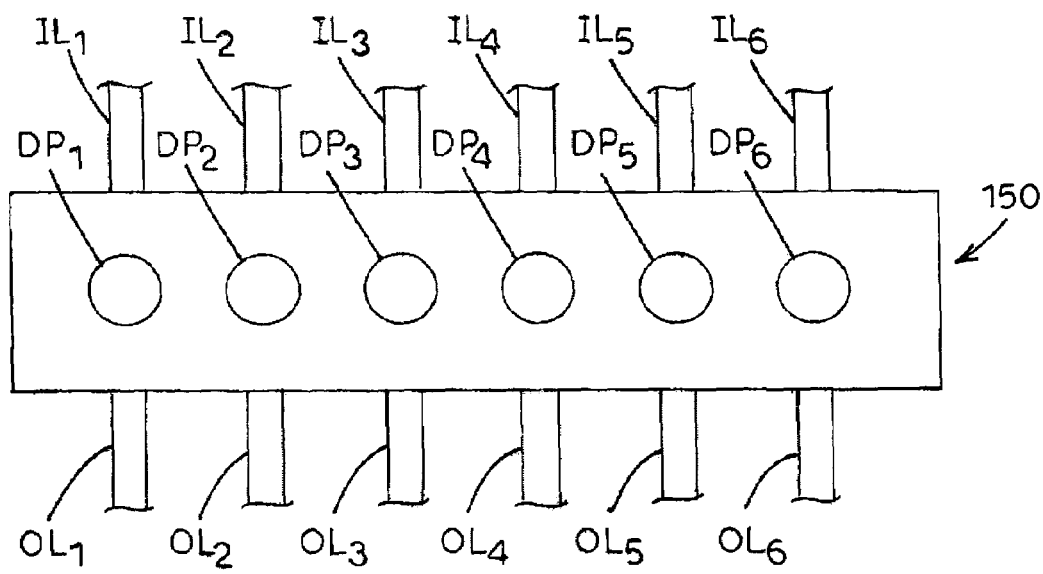
FIG. 4B is a top plan view of the flow cell manifold assembly illustrated in FIG. 4A.
Figure 4C:
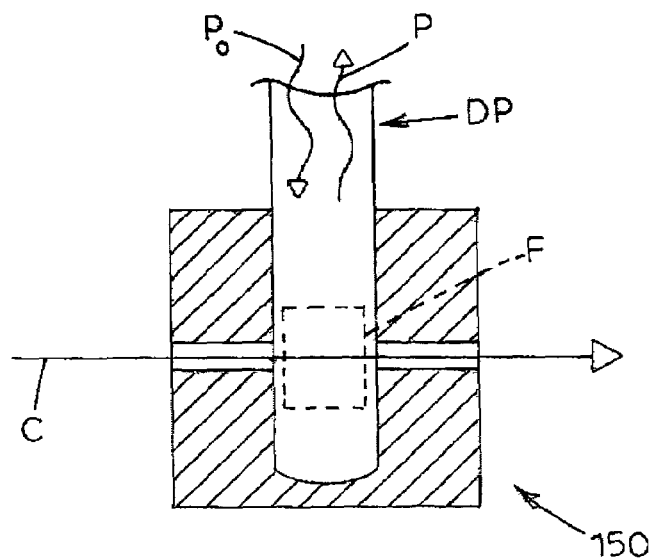
FIG. 4C is a cut-away side elevation view of one of the flow cells of the manifold assembly illustrated in FIGS. 4A and 4B.

Referring now to FIGS. 4A-4C, manifold block 150 according to the present embodiment is a multi-channel device in which a plurality of fiber-optic probes (e.g., six probes $DP_1$-$DP_6$) are removably inserted into the body of manifold block 150. The design of probes $DP_1$-$DP_6$ can be that illustrated in FIG. 3 or can be similar thereto. That is, probes $DP_1$-$DP_6$ can be provided as commercially available dip probes, or can be provided as originally designed probe-like instruments. The structure of manifold block 150 is such that each probe $DP_1$-$DP_6$, when properly inserted, is brought into fluid communication with the media flowing through input lines $IL_1$-$IL_6$ and output lines $OL_1$-$OL_6$ associated with each flow cell $F_1$-$F_6$ of manifold block 150. It should be noted that flow cells F can be defined by the structure of either manifold block 150 or probes $DP_1$-$DP_6$ (as in FIG. 3), depending on the respective designs of manifold block 150 and probes $DP_1$-$DP_6$. As best shown in the cross-sectional view of FIG. 4C, media flows through each channel of manifold block 150 and corresponding flow cell F in the direction indicated by arrow C, while the light beam provided by a light source such as radiation source 73 in FIG. 2 travels in a generally transverse direction. A light beam of initial intensity $P_o$ is sent by way of a fiber-optic guide or cable through flow cell F, and is subsequently reflected back out of flow cell F and returned by way of another fiber-optic guide or cable at an attenuated intensity P.

Figure 5A:
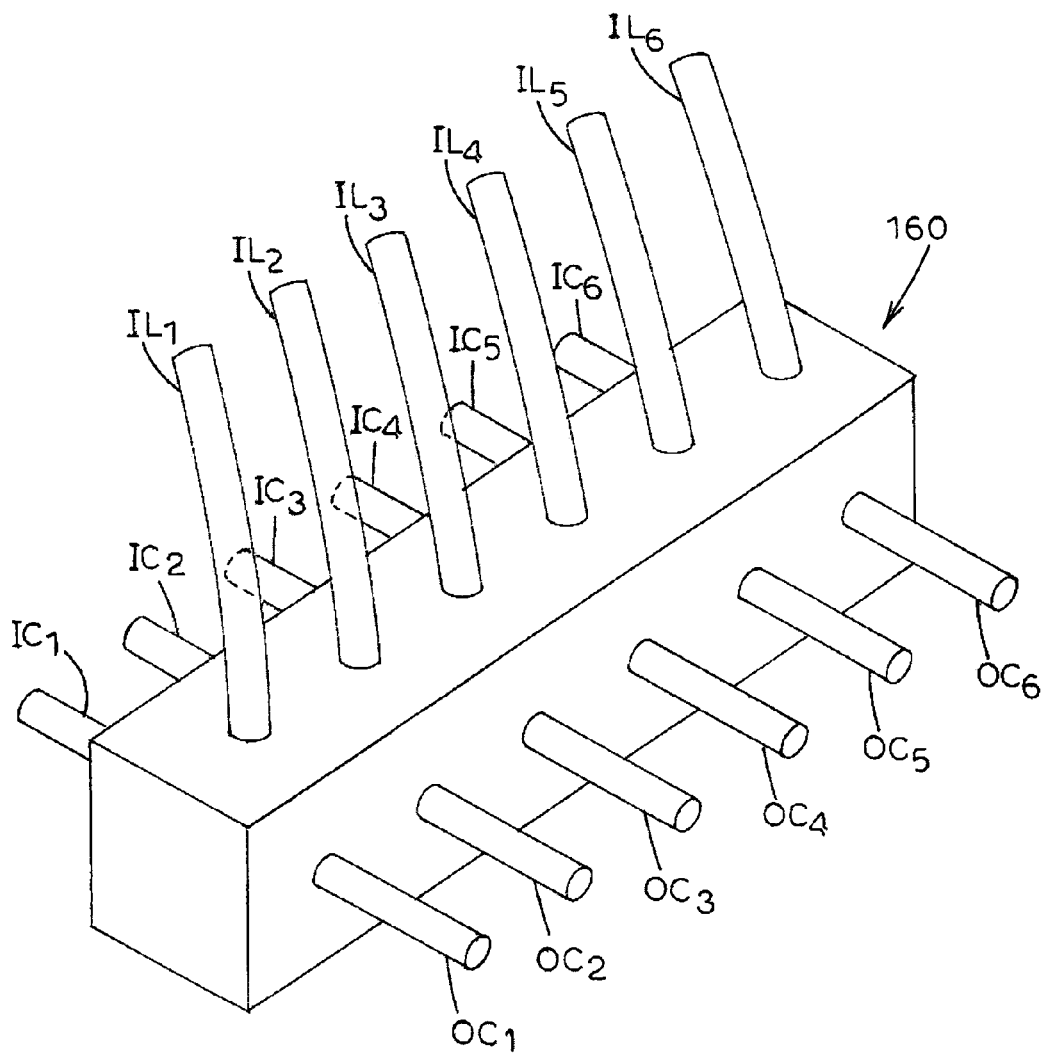
FIG. 5A is a perspective view of a flow cell manifold assembly provided according to another embodiment of the present invention.
Figure 5B:
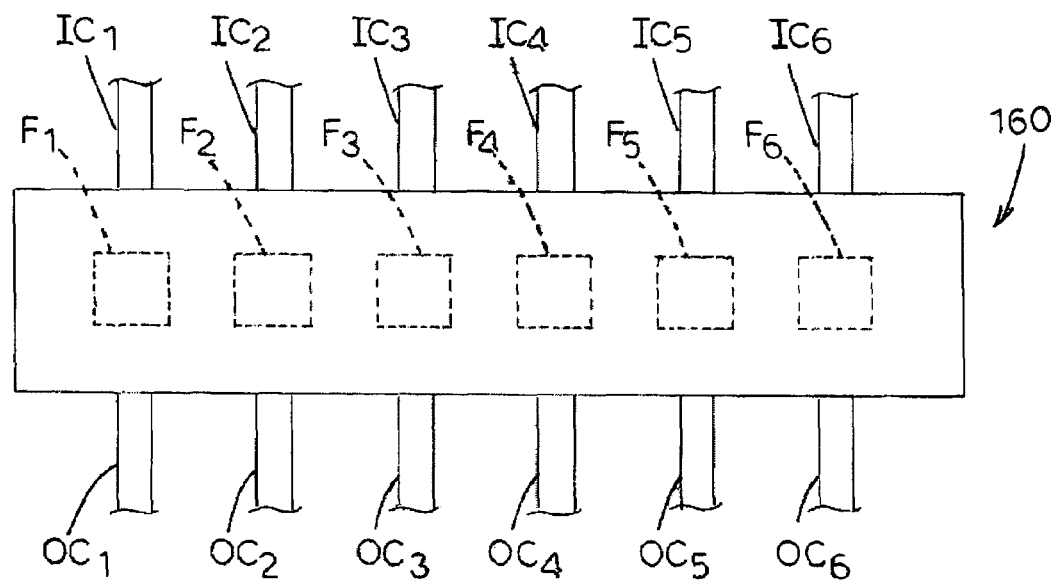
FIG. 5B is a top plan view of the flow cell manifold assembly illustrated in FIG. 5A.
Figure 5C:
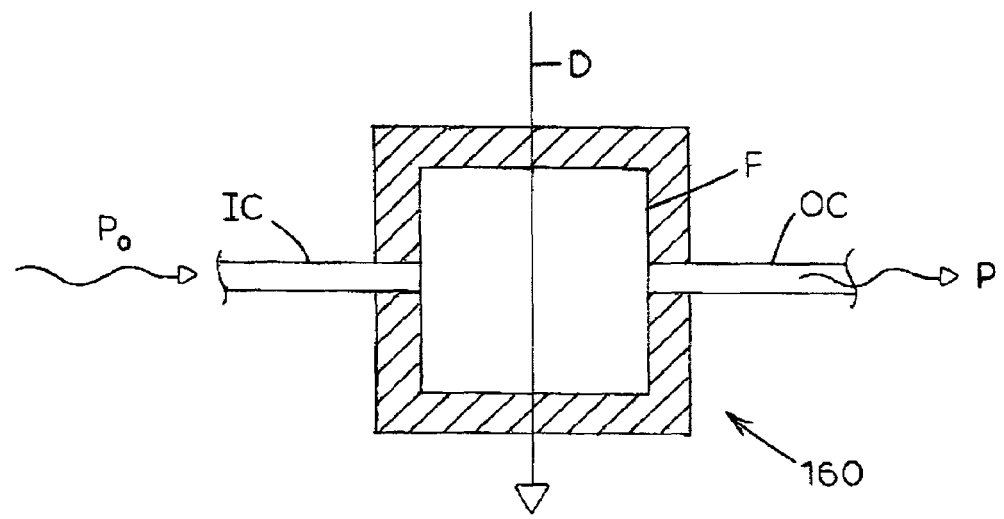
FIG. 5C is a cut-away side elevation view of one of the flow cells of the manifold assembly illustrated in FIGS. 5A and 5B.

Referring now to FIGS. 5A-5C, an alternative manifold block, generally designated 160, is illustrated according to another embodiment of the invention. Manifold block 160 does not require the use of probes $DP_1$-$DP_6$. Instead, manifold block 160 is structured to define a plurality of flow cells $F_1$-$F_6$ (see FIG. 5B). Each flow cell $F_1$-$F_6$ is respectively disposed in fluid communication with a liquid input line $IL_1$-$IL_6$ and a liquid output line $OL_1$-$OL_6$, and further in optical communication with a light input line $IC_1$-$IC_6$ and a light output line $OC_1$-$OC_6$. As best shown in FIG. 5C, light input and output lines IC and OC are opposing fiber-optic cables whose respective glass cores are properly aligned with each other. The respective fiber diameters of input and output lines IC and OC can be same or, alternatively, the fiber diameter of output line OC is larger than that of input line IC. The respective fiber diameters will depend on the optical path length, or gap, between the respective opposing fiber ends of input and output lines IC and OC across which the light radiation must travel through flow cell $F_1$-$F_6$. Hence, for larger optical paths over which a greater amount of diffraction of the radiation energy will occur, a larger diameter for output line OC may be needed. The manner of operation of manifold block 160 in FIGS. 5A-5C, including the generation of analytical signals in each respective flow cell $F_1$-$F_6$, is analogous to that of manifold block 150 illustrated in FIGS. 4A-4C.

Figure 6:
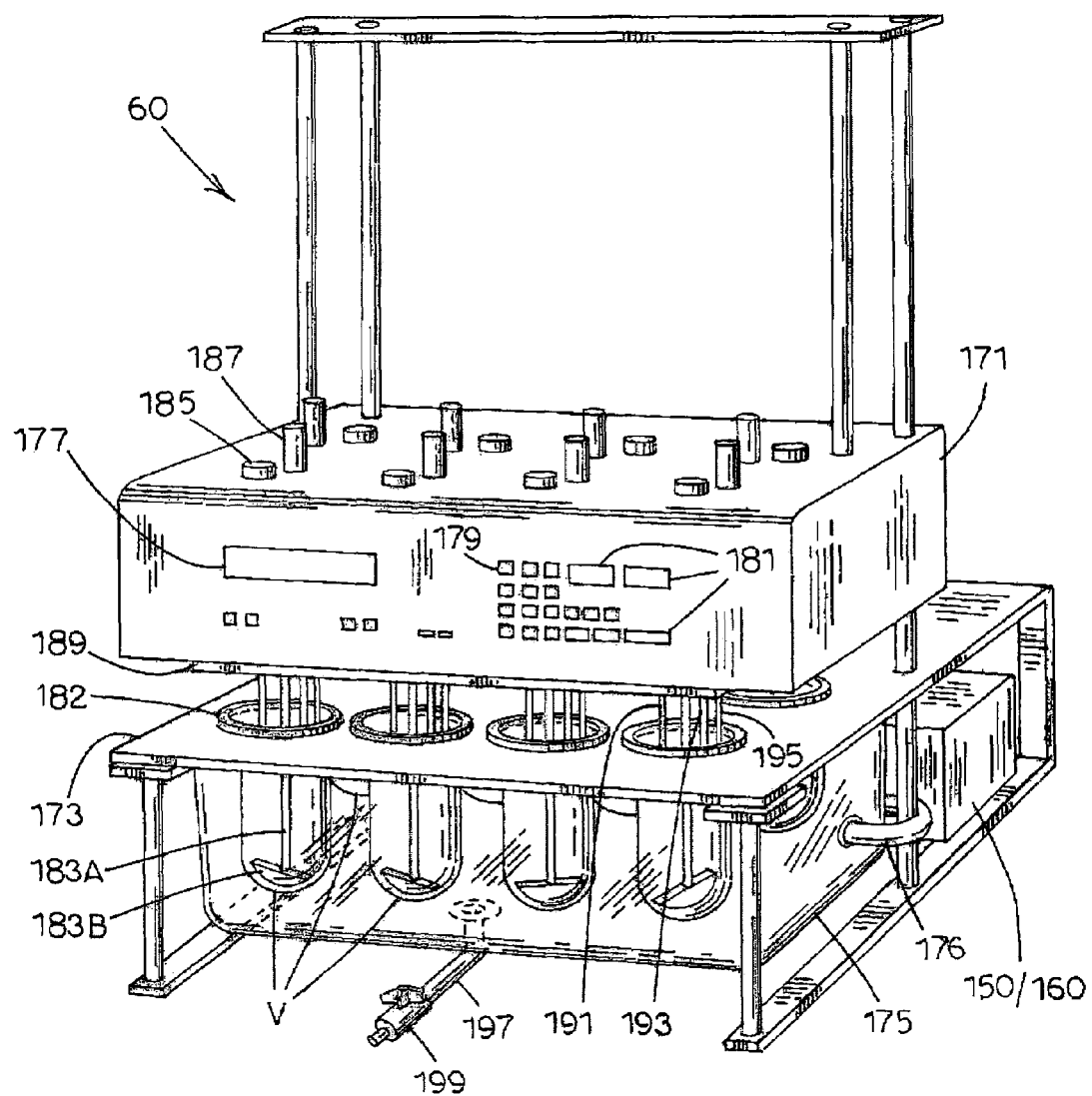
FIG. 6 is a perspective view of a dissolution media preparation and testing apparatus to which is mounted a flow cell manifold assembly according to any of the embodiments of the present invention.

Referring now to FIG. 6, dissolution media preparation/testing apparatus 60 is illustrated in which manifold block 150 or 160 (designed in accordance with any of the embodiments described above) has been mounted "on-board." By way of example, media preparation apparatus 60 includes a main housing or head assembly 171 containing a programmable systems control module. Head assembly 171 is situated above a vessel plate 173 and a water bath container 175, and is typically motor-driven for vertical movement toward and away from vessel plate 173. Peripheral elements located on head 171 include an LCD display 177 for providing menus, status and other information; a keypad 179 for providing user-inputted operation and control of spindle speed, temperature, test start time, test duration and the like; and readouts 181 for displaying information such as RPM, temperature, elapsed run time, or the like. Vessel plate 173 supports a plurality of vessels V extending into the interior of water bath container 175. One of vessels V can be utilized as blank vessel BV, another as standard vessel SV, and the rest as test vessels $V_1$-$V_6$ (see, e.g., FIGS. 1 and 2). A typical top-view arrangement of test vessels $V_1$-$V_6$, blank vessel BV, and standard vessel SV on vessel plate 173 is shown in FIG. 2. Water is heated and circulated through water bath container 175 ordinarily by means such as external heater and pump modules (not shown), which may be combined into a single heater/circulator module. Water bath container 175 thus requires a fluid transfer means such as tubing 176, as well as a drain line 197 and valve 199. Alternatively, media preparation/testing apparatus 60 can be a waterless heating design in which each vessel V is directly heated by some form of heating element disposed in thermal contact with the wall of vessel V.

Vessels V are typically locked and centered in place on vessel plate 173 by means such as ring lock devices or clamps (not shown). A stirring element including a motor-driven spindle 183A and paddle 183B operates in each vessel V. Individual clutches 185 can be provided to alternately engage and disengage power to each spindle 183A. A dosage delivery module 187 is used to preload and drop dosage units (e.g., tablets) into each vessel V at prescribed times and bath (or vessel) temperatures. An automated assembly or sampling manifold 189 lowers and raises sampling cannulas 191 and return cannulas 193 into and out of each respective vessel V. Automated assembly 189 can also be vertically movable between head assembly 171 and vessel plate 173. Sampling cannulas 191 and return cannulas 193 operate in conjunction with a bidirectional peristaltic pump (not shown), and are used during the dissolution testing procedure to periodically withdraw samples from the vessel media for analysis. Samples could also be taken manually using pipettes and/or sampling cannula/syringe assemblies. Miniature temperature probes 195 associated with each vessel V can also be located on automated assembly 189.

In a typical operation, each vessel V is filled with a predetermined volume of dissolution media. Dosage units are dropped either manually or automatically into each media-containing vessel V, and each paddle 183B (or other agitation or USP-type device) is rotated within its vessel V at a predetermined rate and duration within the test solution as the dosage units dissolve. In other types of tests, a cylindrical basket (not shown) loaded with a dosage unit is substituted for each paddle 183B and rotates within the test solution. For any given vessel V, the temperature of the test solution must be maintained at a prescribed temperature (e.g., approximately 37±0.5° C. if certain USP dissolution methods are being conducted). The mixing speed of paddle 183B must also be maintained. Solution temperature is maintained by immersion of vessel V in the water bath of water bath container 175, or alternatively by direct heating as described previously. Accordingly, the temperature of the test solution is dependent upon, and thus indirectly controlled by, the temperature of the water bath which in turn is dictated by the external heating means employed. Temperature probe 195 is used to monitor the test solution temperature, and can be any suitable type of transducer such as a thermistor. Preferably, sampling manifold 189 lowers the various cannulas and probes associated with media preparation/testing apparatus 60 into corresponding vessels V only while samples are being taken at allotted times. At all other times, the cannulas and probes are kept outside of the media contained in vessels V, thereby significantly reducing the turbulence created by whatever cannulas and probes are used. In accordance with the invention described hereinabove and illustrated in FIGS. 1 and 2, sample cannulas 191 and return cannulas 193 are respectively connected to sample lines $SL_1$-$SL_6$, BS and SS and return lines $RL_1$-$RL_6$, BR and SR to integrate dissolution media preparation/testing apparatus 60 with media sampling system 10 and dissolution system 50.

It will be understood that the embodiments described hereinabove can be slightly modified to utilize more than one media preparation/testing apparatus 60, more than one sample analyzing apparatus 70, and/or more than one set of flow cells F.

It is therefore seen from the foregoing description that the present invention provides a number of systems, devices and methods benefiting from the use of fiber-optics and remote flow cells. The embodiments described herein result in high-quality analysis and quantification of analytical samples with decreased effort.

It will be further understood that various details of the invention may be changed without departing from the scope of the invention. Furthermore, the foregoing description is for the purpose of illustration only, and not for the purpose of limitation—the invention being defined by the claims.

What is claimed is:

1. A dissolution test apparatus comprising:
   (a) a frame for supporting a plurality of vessels;
   (b) a plurality of flow cells supported by the frame outside of the vessels, the plurality of flow cells being separate from and remotely positioned from a detector;
   (c) a plurality of media sampling lines for transferring media from one or more respective vessels to one or more of the flow cells;
   (d) a plurality of optical fiber input lines communicating with respective flow cells for transmitting an optical signal to one or more of the flow ceils;
   (e) a plurality of optical fiber output lines communicating with respective flow cells for transmitting an optical signal from one or more of the flow cells to the remotely positioned detector; and
   (f) a plurality of media return lines for transferring media from respective flow ceils to one or more vessels.

2. The apparatus according to claim 1 comprising a manifold mounted to the frame and including the plurality of flow cells.

3. The apparatus according to claim 2 wherein the manifold comprises a manifold body and a plurality of probes at least partially disposed in the body, each probe fluidly communicates with a respective flow cell, and a respective optical fiber input line and optical fiber output line extend in the probe in optical communication with the respective flow cell.

4. The apparatus according to claim 2 wherein each optical fiber input line and corresponding optical fiber output line are mounted at the manifold in opposing relation for providing an optical path through a respective flow cell.

5. The apparatus according to claim 1 comprising a calibration system for selectively transferring calibration media to one or more of the flow cells simultaneously and bypassing the vessels corresponding to the one or more flow cells.

6. A dissolution test system comprising:
(a) a plurality of test vessels for holding test media;
(b) a plurality of flow cells defining respective optical paths through the flow cells for optical communication with a detector situated remotely from the test vessels, and respective fluid paths through the flow cells for fluid communication with the test vessels, the plurality of flow cells situated outside of the test vessels and being separate from and remotely positioned from the detector;
(c) a calibration vessel for holding calibration media;
(d) a fluid distribution system for selectively transferring test media from one or more of the test vessels to one or more respective flow cells and, alternately, transferring calibration media from the calibration vessel to more than one flow cell simultaneously, wherein the fluid distribution system comprises a plurality of test media sampling lines communicating with respective test vessels; and
(e) a plurality of media return lines for transferring media from respective flow ceils to one or more vessels.

7. The system according to claim 6 comprising a dissolution test apparatus, wherein the test vessels and flow cells are positioned at the dissolution test apparatus.

8. The system according to claim 6 comprising a plurality of optical input fibers communicating with respective flow cells and a plurality of optical output fibers communicating with respective flow cells.

9. The system according to claim 8 comprising a manifold including the flow cells and a plurality of probes at least partially extending into the manifold and communicating with respective flow cells, wherein one of the optical input fibers and a corresponding one of the optical output fibers extend into each probe.

10. The system according to claim 8 comprising a manifold including the flow cells, wherein each optical input fiber and corresponding optical output fiber are mounted at the manifold in opposing relation for providing the optical path through a respective flow cell.

11. The system according to claim 6 comprising a dissolution test apparatus supporting the test vessels and a manifold, wherein the manifold includes the flow cells and is mounted to the dissolution test apparatus.

12. The system according to claim 6 wherein the fluid distribution system comprises a plurality of valves for selectively switching between a plurality of sampling flow paths defined from the test vessels to respective flow cells and a plurality of calibration flow paths defined from the calibration vessel to respective flow cells.

13. The system according to claim 6 further comprises a plurality of calibration media sampling lines communicating with the calibration vessel, a plurality of first valves selectively providing communication between respective test media sampling lines and flow cells and alternately between respective calibration media sampling lines and flow cells, a plurality of bypass lines communicating with the calibration vessel, and a plurality of second valves selectively providing communication between respective flow cells and test vessels and alternately between respective flow cells and bypass lines for bypassing the test vessels.

14. The apparatus according to claim 1, wherein the frame includes a vessel plate having a plurality of apertures for receiving the plurality of respective vessels, and the plurality of media sampling lines includes a plurality of respective sampling cannulas, each sampling cannula supported by the frame and insertable through and removable from a respective aperture for aspirating media from a vessel supported in the respective aperture.

15. The apparatus according to claim 14, further including a plurality of media return lines communicating with respective flow cells and including a plurality of respective return cannulas, each return cannula supported by the frame and insertable through and removable from a respective aperture for transferring media from the respective flow cells to one or more vessels.

16. The apparatus according to claim 1, further including a plurality of sampling circuits located at the frame and remotely positioned from the detector, each sampling circuit including a respective media sampling line, a flow cell, and a media return line for transferring media from the respective flow cell to a corresponding vessel.

17. The system according to claim 6, further including a vessel support structure for supporting the plurality of test vessels, and wherein the fluid distribution system includes a plurality of media sampling lines including a plurality of respective sampling cannulas, each sampling cannula insertable into and removable from a respective test vessel supported by the vessel support structure for aspirating media from the test vessel.

18. The system according to claim 17, wherein the fluid distribution system further includes a plurality of media return lines communicating with respective flow cells, the plurality of media return lines including a plurality of respective return cannulas, each return cannula insertable into and removable from a respective test vessel for transferring media from the respective flow cells to one or more test vessels.

19. The system according to claim 6, further including:
a dissolution test apparatus supporting the plurality of flow cells and the plurality of test vessels;
a liquid circuit located at the dissolution test apparatus and remotely positioned from the detector, the liquid circuit including the plurality of flow cells, the plurality of test vessels, a plurality of test media sampling lines for transferring media from one or more respective test vessels to one or more respective flow cells, and a plurality of media return lines for transferring media from one or more respective flow cells to one or more respective test vessels; and
an optical circuit including the plurality of flow cells, a plurality of optical fiber input lines communicating with respective flow cells for transmitting an optical signal to one or more of the flow cells, and a plurality of optical fiber output lines communicating with respective flow cells for transmitting an optical signal from one or more of the flow cells to the remotely positioned detector.

20. A method for conducting a dissolution test on a sample, comprising:
(a) transferring analyte-containing liquid samples from a plurality of respective test vessels supported by a dissolution test apparatus, through a plurality of corresponding test media sample lines, and through a plurality of corresponding flow cells, the flow cells being located at the dissolution test apparatus outside of the test vessels and remote from a detector;
(b) transmitting a plurality of incident optical signals through the plurality of corresponding flow cells to produce a plurality of corresponding resultant optical signals;
(c) transmitting the plurality of corresponding resultant optical signals to the remotely-positioned detector to acquire data indicative of a concentration of analytes in the respective liquid samples; and
(d) after transmitting the plurality of incident optical signals, transferring the liquid samples from the plurality of corresponding flow cells through a plurality of corresponding test media return lines, and back to the respective test vessels.

21. The method according to claim 20 further including, before transferring the analyte-containing liquid samples from the plurality of respective test vessels, inserting a plurality of sampling cannulas of corresponding test media sample lines into the respective test vessels, and after transferring the analyte-containing liquid samples from the plurality of respective test vessels, removing the plurality of sampling cannulas from the respective test vessels.

22. The method according to claim 20 further including transferring a calibration fluid from a calibration vessel to each flow cell simultaneously.

* * * * *